United States Patent [19]

Clayberger et al.

[11] Patent Number: 5,620,956
[45] Date of Patent: Apr. 15, 1997

[54] METHODS OF USING CD8 BINDING DOMAIN PEPTIDES

[75] Inventors: Carol Clayberger; Alan M. Krensky, both of Stanford, Calif.

[73] Assignee: The Board of Regents of the Leland Stanford Junior University, Stanford, Calif.

[21] Appl. No.: 279,501

[22] Filed: Jul. 22, 1994

Related U.S. Application Data

[63] Continuation of Ser. No. 791,925, Nov. 8, 1991, abandoned.

[51] Int. Cl.$^6$ .......................... A61K 38/00; A61K 38/02; C07K 5/00; C07K 7/00
[52] U.S. Cl. ........................... 514/14; 514/15; 514/16; 435/7.1; 435/377; 530/300; 530/327; 530/328; 530/329
[58] Field of Search ................... 514/14, 15, 16, 514/885; 530/300, 327, 328, 329; 435/1, 7.1

[56] References Cited

PUBLICATIONS

Krensky et al., *Transplantation Proceedings*, vol. 25, No. 1, Feb. 1993, pp. 483–484.
Karaki et al., *Journal of Immunology*, vol. 149, No. 5, pp. 1613–1618, Sep. 1, 1992.
König et al., *Nature*, vol. 356, pp. 796–798, 30 Apr. 1992.
Tanabe et al., *Journal of Immunology*, vol. 148, No. 10, pp. 3202–3209, May 15, 1992.
Salter et al., *Nature*, vol. 345, pp. 41–46, 3 May 1990.
Potter et al., *Nature*, vol. 357, pp. 73–75, 5 Jan. 1989.
Connolly et al., *P.N.A.S.*, pp. 2137–2141, Mar. 1990.

*Primary Examiner*—Avis M. Davenport
*Attorney, Agent, or Firm*—Morrison & Foerster LLP

[57] ABSTRACT

The present invention provides compositions comprising a peptide having between about 7 and about 20 amino acid residues, the peptide being capable of binding a CD8 molecule on a cytolytic T lymphocyte (CTL) precursor and inhibiting differentiation of the CTL precursor to a mature CTL. The peptides have amino acid sequences substantially homologous to a sequence in an α3 domain of a human Class I MHC molecule. The sequence from the α3 domain is preferably between residue 220 and residue 235. The peptides typically comprise the sequences DQTQDTE (SEQ. ID No. 1) or EDQTQDTELVETRP (SEQ. ID No. 2).

5 Claims, 3 Drawing Sheets

FIG.-3

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp Gln Thr Gln Asp Thr Glu
    1               5

( 2 ) INFORMATION FOR SEQ ID NO:2:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:2:

Glu Asp Gln Thr Gln Asp Thr Glu Leu Val Glu Thr Arg Pro
    1               5                   1 0

METHODS OF USING CD8 BINDING DOMAIN PEPTIDES

This is a continuation of application Ser. No. 07/791,925 filed Nov. 8, 1991 and now abandoned.

FIELD OF THE INVENTION

The invention relates to HLA peptide compositions which affect T-cell activity. Methods and compositions are provided for the modulation of cytolytic T-lymphocyte activity.

BACKGROUND OF THE INVENTION

Cytolytic T-lymphocytes (also called "cytotoxic T-lymphocytes," and typically abbreviated "CTLs") are a class of T-cells that adhere to and lyse target cells. Most CTLs are restricted in their targeting activity by recognizing, on the surface of a target cell, a Class I major histocompatibility molecule (Class I MHC) bearing an associated antigen. Interaction between the CTL and its target is believed to be mediated by adhesion of a T-cell receptor (TCR) and an associated complex of proteins known as "CD3" (together referred to as the "TCR:CD3" complex), with an MHC-antigen complex on the target cell. CTLs, which interact with Class I MHC molecules, frequently possess another accessory protein called "CD8." CD8 is thought to be a CTL surface glycoprotein that facilitates the interaction between the TCR:CD3 complex and the MHC:antigen complex. CD8 binds to a region on the Class I MHC molecule different from the TCR:CD3 binding site and enhances adhesion. The CD8 molecule is also involved in mediating signal transduction and otherwise modulating the functional responses that accompany binding of the CTL to its target.

One of the primary functions of the CTL system is to destroy cells which are producing foreign antigens, such as cells infected with a virus. However, CTLs are also involved in the destruction of foreign cells that were purposely introduced into the body as grafts or transplants from allogeneic hosts. This process, known as "allograft rejection," involves the interaction of host CTLs with foreign MHC molecules. The most commonly used approach to preventing allograft rejection is to suppress the immune system in the recipient; typically by using immunosuppressive drugs. However, use of these drugs can cause severe side effects including nephrotoxicity, hypertension, bone loss and lymphoma. Another approach has been the use of antibodies to human T-cells, such as OKT3 and OKT4. However, problems have been encountered with that approach because humans mount antibody responses against the proteins, rendering them ineffective.

There remains a substantial need for ways to control the cytolytic system in a host by selectively modulating T-cell activities. Major improvements in tissue transplantation could be obtained with the development of more specific, less toxic therapies to prevent allograft rejection.

SUMMARY OF THE INVENTION

The present invention provides compositions comprising a peptide having between about 7 and about 20 residues, the peptide having sequences substantially homologous to an amino acid sequence in an α3 domain of a human Class I MHC molecule. The peptide selectively binds a CD8 molecule on a cytolytic T lymphocyte (CTL) precursor and inhibits differentiation of the CTL precursor to a mature CTL. The sequence from the α3 domain is preferably between residue 220 and residue 235. The peptides typically comprise the sequences DQTQDTE (SEQ. ID No. 1) or EDQTQDTELVETRP (SEQ. ID No. 2).

The invention also relates to pharmaceutical compositions comprising a pharmaceutically acceptable carrier and the peptides described above, as well as methods for modulating the activity of CTLs in a patient. The compositions and methods may be used to treat, for example, allograft rejection. In these compositions the peptide may comprise a D-amino acid.

Also provided are ligands which bind to a CD8 molecule of a CTL precursor and affect differentiation of the CTL precursor to a mature CTL. These ligands can be identified by the ability to compete with the peptides described above for binding to the CD8 molecule. Suitable ligands include peptides and their conformational analogues as well as immunoglobulins.

DESCRIPTION OF THE PREFERRED EMBODIMENT

Methods and compositions are provided for modulating the effects of cytolytic T-lymphocytes. Different Class I MHC molecules, in conjunction with an associated protein antigen, are able to bind to TCR:CD3 complexes on CTLs. Variable regions exist on both the TCR and the class I MHC molecule and are likely to be involved in the specificity of CTL targeting. As discussed above, the CD8 glycoprotein on the CTL surface is an accessory molecule involved in the interaction between CTLs and their targets.

Unlike the TCR, the CD8 molecule is generally invariant within an animal species. Residues 215 to 239 of the α3 domain of MHC Class I molecules are highly conserved, with only four differences between the rat and human molecules:

|       | 215   | 220   | 225   | 230   | 235   |
|-------|-------|-------|-------|-------|-------|
| Rat   | LTWQL | NGEDL | TQDME | LVETR | PAGDG |
| Human | LTWQR | DGEDQ | TQDTE | LVETR | PAGDG |

As is described below, polypeptides comprising portions of this highly conserved region, including for example the 14-mer EDQTQ DTELV ETRP (SEQ. ID No. 2) (corresponding to residues 222–235), are used to modulate the interactions between CTLs and their targets.

A preferred modulation of CTL function is the inhibition of CTL differentiation. Mature CTLs differentiate from "pre-CTLs" present in the blood and peripheral lymphoid tissues. Pre-CTLs have already undergone thymic maturation and are specific for a particular foreign antigen but lack cytolytic function. The first step in differentiation or "activation" is the binding of the pre-CTL to foreign antigen.

This interaction with foreign antigen renders the CTL responsive to cytokines, which are involved in completion of the differentiation process The term "differentiation" as used herein, encompasses the process of maturation from a pre-CTL to a mature CTL. The presence of mature CTLs can be detected in a number of ways, as described below. They are typically detected by their ability to lyse appropriate antigen presenting cells. For a discussion of the events involved in CTL differentiation, see, e.g., Abbas, A., et al., *Cellular and Molecular Immunology,* W. B. Saunders (1991), which is incorporated herein by reference.

Polypeptides suitable for use in the present invention can be obtained in a variety of ways. Conveniently, they can be synthesized by conventional techniques employing automatic synthesizers, such as the Beckman, Applied Biosystems, or other commonly available peptide synthesizers using well known protocols. They can also be synthesized manually using techniques well known in the art. See, e.g. Stewart and Young, *Solid Phase Peptide Synthesis,* Rockford, Ill., Pierce, 2d Ed. (1984), which is incorporated herein by reference.

Alternatively, DNA sequences which encode a protein comprising the particular peptide may be cloned and expressed to provide the peptide. Cells comprising a variety of MHC genes are readily available, for instance, they may be obtained from the American Type Culture Collection ("Catalogue of Cell Lines and Hybridomas," 6th edition (1988) Rockville, Md., U.S.A. For instance, standard techniques can be used to screen cDNA libraries to identify sequences encoding the desired sequences (see, Sambrook et al., *Molecular Cloning—A Laboratory Manual,* Cold Spring Harbor Laboratory, Cold Spring Harbor, N.Y., 1989, which is incorporated herein by reference). For instance, fusion proteins (those consisting of all or part of the amino acid sequences of two or more proteins) can be recombinantly produced. In addition, using in vitro mutagenesis techniques, unrelated protein can be mutated to comprise the appropriate CD8 binding sequences.

MHC class I glycoproteins from a variety of natural sources are also conveniently isolated using standard protein purification techniques. Peptides can be purified by any of a variety of known techniques, including, for example, reverse phase high-performance liquid chromatography (HPLC), ionexchange or immunoaffinity chromatography, separation by size, or electrophoresis (see, generally, Scopes, R., *Protein Purification,* Springer-Verlag, N.Y. (1982), which is incorporated herein by reference).

Although relatively short peptide fragments are preferred in the present invention, in certain cases it may desirable to use larger polypeptides (greater than about 30 residues) comprising the sequences disclosed here. As used herein, a "polypeptide" or "peptide" is a molecular chain of residues linked by peptide bonds (or peptide bond mimetics). The term also encompasses protein molecules (e.g., fusion proteins), or portions thereof, which include the CD8 binding sequences. The term "residue" refers to an amino acid (D- or L-) or amino acid mimetic incorporated in a polypeptide or peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins,* Vol. VII (Weinstein ed,, 1983), which is incorporated herein by reference. Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH=CH]$. The nomenclature used above, follows that suggested by Spatola, supra. In this context, $\psi$ indicates the absence of an amide bond. The structure that replaces the amide group is specified within the brackets.

An "amino acid mimetic" as used herein is a moiety other than a naturally occurring amino acid that conformationally and functionally serves as a substitute for an amino acid in a peptide of the present invention. Such a moiety serves as a substitute for an amino acid residue if it does not interfere with the ability of the peptide to bind to CD8. Amino acid mimetics may include non-protein amino acids, such as β-γ-δ-amino acids, β-γ-δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, *Ann. Repts. Med. Chem.* 24:243–252 (1989), which is incorporated herein by reference.

Thus, a number of conformational analogues of the amino acid sequences in the α3 domain identified above can be used to modulate CTL function. The ability of the analogues to bind CD8 and modulate CTL function can be tested in the assays described below. As used herein, "conformational analogues" are molecules having spatial or polar organization sufficiently similar to the amino acid sequences of the α3 domain that specific binding of the CD8 molecule occurs. Like other specific binding interactions, recognition will typically include reversible noncovalent associations such as electrostatic attraction, Van der Waals forces, and hydrogen bonds. The conformational analogues of the invention may consist entirely of amino acid residues other than those found in the α3 sequence. Alternatively, they may comprise any of a number of amino acid mimetics linked by peptide bond mimetics.

The peptides and their analogues typically comprise at least about 7 residues and more preferably at least about 13 residues. Preferably, they will not exceed about 30 residues and, more preferably, they will not exceed about 20 residues.

The peptides or polypeptides of the invention can be modified in a number of ways so long as they comprise a sequence substantially homologous to a sequence in the α3 domain of an MHC Class I molecule. As used herein "substantially homologous" means that the percentage of identical residues at corresponding positions in two sequences is at least about 40%, usually about 75%, and preferably about 95% or more. Two residues are considered to be identical if the residues are the same (D- and L-isomers of a particular amino acid are considered to be the same residue) or if one residue is a mimetic of the other, as defined above.

In addition to peptides, polypeptides, and their analogues, various other ligand molecules recognized by CD8 can be used to modulate CTL function. For instance, immunoglobulins which bind either CD8 or the appropriate sequences in the α3 domain may also be used to block interactions between MHC molecules and CD8. For instance, antibodies to the α3 domain of class I MHC molecules (e.g., 34-2-12S, described in Ozato et al., *Transplantation* 34:113 (1982), which is incorporated herein by reference) can be used.

The multitude of techniques available to those skilled in the art for production and manipulation of various immunoglobulin molecules can thus be readily applied to inhibit adhesion of leukocytes to myelin sheaths. As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. Immunoglobulins may exist in a variety of forms besides antibodies, including for example, Fv, Fab, and F(ab)$_2$, as well as in single chains (e.g., Huston et al., *Proc. Nat. Acad. Sci. U.S.A.* 85:5879–5883 (1988) and Bird et al., *Science* 242:423–426 (1988), and Hunkapiller and Hood, *Nature* 323:15–16 (1986), which are incorporated herein by reference). For a general review of immunoglobulin structure and function see, *Fundamental Immunology*, 2d Ed., W. E. Paul ed., Ravens Press, N.Y., (1989) which is incorporated herein by reference.

Antibodies which bind either CD8 or the α3 domain may be produced by a variety of means. The production of non-human monoclonal antibodies, e,g., murine, lagomorpha, equine, etc., is well known and may be accomplished by, for example, immunizing the animal with a preparation containing CD8 or the appropriate sequence from the α3 domain. Antibody-producing cells obtained from the immunized animals are immortalized and screened, or screened first for the production of antibody which inhibits binding between MHC molecules and CD8 and then immortalized. For a discussion of general procedures of monoclonal antibody production see Harlow and Lane, *Antibodies, A Laboratory Manual*, Cold Spring Harbor Publications, N.Y. (1988), which is incorporated herein by reference.

The generation of human monoclonal antibodies to a human antigen may be difficult with conventional techniques. Thus, it may be desirable to transfer the antigen binding regions of the non-human antibodies, e.g., the F(ab')2 or hypervariable regions, to human constant regions (Fc) or framework regions by recombinant DNA techniques to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences which encode a human monoclonal antibody or portions thereof that specifically bind to CD8 or the α3 domain by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

Immunoglobulins which inhibit the binding of MHC molecules to CD8 may also be useful in the generation of anti-idiotypic immunoglobulins. Anti-idiotype immunoglobulins may be produced by, for example, immunization of an animal with the primary immunoglobulin. In the case of immunoglobulins to the α3 domain those anti-idiotype immunoglobulins whose binding to the primary immunoglobulin is inhibited by peptides of the invention are selected. Since both the anti-idiotypic immunoglobulin and the peptides bind the primary immunoglobulin, the anti-idiotypic immunoglobulin may represent the "internal image" of an epitope and thus may substitute for the α3 domain and be used, for example, as an immunogenic reagent.

The modified peptides and other conformational analogues can be assayed for biological activity in a number of different ways. If the CTL function to be modulated is differentiation to mature CTLs, the assays typically involve the detection of mature CTLs by their ability to lyse appropriate antigen presenting cells. The assays in an exemplary protocol described below, involve a limiting dilution analysis to measure the effects of added peptides on CTL differentiation in an in vitro assay using peripheral blood lymphocytes.

The ability of peptides to modulate CTL activity in vitro may then be correlated with the ability to affect the immune response in vivo. In vivo activity is typically assayed using suitable animal models such as rats. The sequence of the rat α3 domain is known and, as discussed above, the sequence from residue 215 to 239 is quite similar to the human sequence. To assay the effect of the peptides on allograft rejection, for example, allogeneic cells might be introduced into an animal following or concurrent with administration of various concentrations of the HLA peptides and suitable controls. Controls may include, for example, synthetic peptides containing the same residues as the test peptides, but arranged randomly. The immune response to the allogeneic cells may be measured by, for example, limiting dilution assays as described below.

Animal models can also be used to directly assay the ability of the peptides to inhibit allograft rejection. For example, the peptides may be administered to the animals at various times before introduction of the allogeneic tissue; and the animals can be monitored for graft rejection. Testing may also be performed in primates using, for example, cynomolgus monkeys. Suitable methods for performing the transplant and monitoring for graft rejection are well known to the skilled artisan (see, e.g., Hislop et al., *J. Thorac. Cardiovasc. Surg.,* 100:360–370 (1990), which is incorporated herein by reference.

The sequences are conveniently modified in a variety of ways depending upon their ultimate purpose. For instance, the effect of single amino acid substitutions may also be probed using D-amino acids or amino acid mimetics. Residue substitutions which lead to increased binding affinity of the peptides can then be identified. The assays of the present invention are conveniently used to identify peptides having increased affinity for CD8 molecules by, for instance, using competition assays to determine concentrations of peptides required to produce 50% inhibition of binding between CD8 and the appropriate MHC molecule.

A core binding domain can be identified by making a series of related peptides which differ from the native-type peptide by one or more substitutions, additions or deletions of residues using techniques well known in the art. The substitutions can screened for their effect on binding by, for example, using a limiting dilution assay or a competition assay with unsubstituted peptides. For instance, a description of various point mutations in genes encoding the α3 domain by Salter, R. D., et al. (*Nature,* 345:41 (1990), which is incorporated herein by reference), provides evidence that several clusters of residues are involved in the interaction with CD8. One cluster includes positions 223–229, which form an exposed loop between strands 3 and 4 of the α3 domain. The sequence from positions 220–232, which includes the exposed loop, contains no basic residues, contains 6 acidic residues (220, 222, 223, 227,229 and 232) and is highly conserved. A second cluster involves residues 233 and 235, which are in the fourth strand of the beta-pleated sheet. The threonine at position 233 is on the exposed surface of the α3 domain, and even fairly conservative changes, to alanine or isoleucine for example, may directly affect binding to CD8. A third cluster involves positions 245 and 247, which are located on the fifth strand of beta-pleated sheet behind the residues making up the first cluster described above.

Besides modifications that affect the interaction with CD8, the peptides and their analogues can be modified to alter, for example, their in vivo stability. For instance, inclusion of one or more D-amino acids in the peptide typically increases stability, particularly if the D-amino acid residues are substituted at one or both termini of the peptide sequence. Stability can be assayed in a variety of ways such as by measuring the half-life of the proteins during incubation with peptidases or human plasma or serum. A number of such protein stability assays have been described (see, e.g., Verhoef et al., *Eur. J. Drug Metab. Pharmacokin.* 11:291–302 (1986), which is incorporated herein by reference), The peptides can also be modified by linkage to other molecules. For example, different N- or C-terminal groups may be introduced to alter the molecule's physical and/or chemical properties. Such alterations may be utilized to affect, for example, adhesion, stability, bio-availability, localization or detection of the molecules. For diagnostic purposes, a wide variety of labels may be linked to the terminus, which may provide, directly or indirectly, a detectable signal. Thus, the peptides of the subject invention may be modified in a variety of ways for a variety of end purposes while still retaining biological activity.

Various reactive sites may be introduced at the terminus for linking to particles, solid substrates, macromolecules, or the like. For example, an internal amino moiety of a growing chain bound to a solid substrate with the intermediate side groups protected, may be conjugated with methyldithiobenzoic acid (MDTB). The free mercaptan group may then be used for conjugating with activated olefins. Thus, proteins, such as serum albumin, keyhole limpet hemocyanin, bovine B-globulin, or the like, may be conjugated to the peptide to provide for an immunogen to produce antibodies to the peptide for use in immunoassays, for affinity chromatography, or the like. Alternatively, the peptide can be bonded to another polypeptide by preparing a DNA sequence which has the peptide at the N-terminus, C-terminus or internal to the protein, so as to provide a fused protein which includes the binding peptide of interest. In this manner, fused proteins may be produced which have enzymatic activity, which enzymatic activity may be modulated by macromolecules.

The subject peptides may be used for modulating CTL activity in a mammalian host, preferably in a human. In one embodiment, the peptides can be used to inhibit the differentiation of CTL precursors into mature CTLs as an approach to inhibiting allograft rejection. Differentiation of CTLs may be assayed using a limiting dilution analysis (LDA), as described in an example below. Since the peptides are more selective and generally less toxic than conventional immuno-modulating agents, they will be less likely to cause the side effects frequently observed with the conventional agents. Also, because the peptides correspond to human protein sequences, they are less likely to cause immunological responses such as those observed with the use of murine anti CD3 antibodies. The peptides of the present invention can also be combined with these traditional therapeutics, and may be used to lower the dose of such agents to levels below those associated with side effects.

A related use for the present invention is in modulating the immune response involved in "graft versus host" disease (GVHD). GVHD is a potentially fatal disease which occurs when immunologically competent cells are transferred to an allogeneic recipient. If the donor's immunocompetent cells are not inactivated by the recipient host (in an immunosuppressed individual, for example), then these donor cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. Applied in the GVHD context, the peptides of the present invention are used to block the binding domain on the CD8 molecules of the donor CTLs, thereby interfering with their ability to lyse target cells in the host.

The usefulness of the peptides of the present invention is not limited to therapeutics for allograft rejection and graft versus host disease. For instance, the present invention is also useful in any circumstance in which it is desirable to block or modulate the interaction between CD8 and Class I MHC molecules such as allergic responses, autoimmune responses and the like.

In addition, the present invention is useful for preventing an immune response in the context of certain somatic gene therapies. Although gene therapy may involve correction of an individual's own cells, and thus does not present the same problem as allograft rejection (in which foreign MHC molecules are involved), the expression of foreign proteins might trigger a CTL-mediated immune response which could jeopardize treatment. In the context of gene therapy, an individual's own cells might be modified to enable production of a new protein so as to correct, for example, an inborn error of metabolism resulting in the loss or modification of an essential protein. The approach might be circumvented if the recipient's CTLs reacted against cells expressing the new protein. The present invention is useful to inhibit that recognition by interfering with the interaction between CD8 and the MHC molecule presenting the "foreign" antigen.

Peptides of the present invention can also be used to target CTLs. In this context, the peptides are typically conjugated to another molecule. For example, the peptides can be joined to liposomes containing particular immunosuppressive agents, to a specific monoclonal antibody or immunoglobulin, or to a cytotoxin or other modulator of cellular activity, whereby binding of the conjugate to the CTL will result in alteration of the CTL. For example, a number of protein toxins are well known in the art including ricin, diphtheria, gelonin, Pseudomonas toxin, and abrin. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the target T-cells.

The peptides of the present invention can also be used to label cytolytic T-lymphocytes. Labelling of CTLs, which may be useful for diagnostic purposes, can be achieved by linking any of a wide variety of known labels to the peptide. After exposure of the labelled peptide to the CTLs, labelled CTLs can be detected either directly or indirectly. For example, fluorescers, enzymes or other detectable molecules may be joined to the peptides of the present invention. These detectable molecules may be linked directly the CTL-modulating peptide or indirectly through other molecules. For example, biotin introduced into the peptide will subsequently bind to an avidin conjugate with enzymes or fluorescers. Fluorescent labelling can be useful, for example, by allowing CTLs to be detected in a fluorescence activated cell sorter (FACS). A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, etc. Those of ordinary skill in the art will know of other suitable labels for binding to the complexes, or will be able to ascertain such using routine experimentation. The binding of these labels is achieved using standard techniques common to those of ordinary skill in the art.

In vitro uses include, diagnostic applications, isolating or labeling specific cells, and the like. For instance, the peptides of the present invention can be used to assay for potential inhibitors of MHC-T cell interactions. Potential inhibitors can be assayed for the ability to inhibit binding of the peptides to isolated CD8.

Labelling CTLs in vivo may be useful, for example, for monitoring the presence and concentration of CTLs at particular locations in the organism. For in vivo diagnostic imaging, radioisotopes are typically used in accordance with well known techniques. The radioisotopes may be bound to the protein or peptide either directly or indirectly using intermediate functional groups which were well known to those skilled in the art at the time the parent application was filed. For instance, chelating agents such as diethylenetriaminepentacetic acid (DTPA) and ethylenediaminetetraacetic acid (EDTA) and similar molecules have been used to bind proteins to metallic ion radioisotopes.

The peptides can also be labeled with a paramagnetic isotope for purposes of in vivo diagnosis, as in magnetic resonance imaging (MRI) or electron spin resonance (ESR), both of which were well known at the time the parent application was filed. For instance, these and related techniques have been used in the diagnosis of rheumatic diseases (see, Namey, in *Textbook of Rheumatology*, Kelley et al (eds.) Saunders, Philadelphia, 1985, which is incorporated herein by reference). In general, any conventional method for visualizing diagnostic imaging can be used. Usually gamma and positron emitting radioisotopes are used for camera imaging and paramagnetic isotopes are used for MRI. Thus, the peptides of the present invention can be used to monitor the course of amelioration of an autoimmune response in an individual. By measuring the increase or decrease in the number of CTLs it is possible to determine whether a particular therapeutic regimen aimed at ameliorating the deleterious CTL activity is effective.

The peptides are particularly useful in therapeutic applications. Pharmaceutical compositions of the invention are suitable for use in a variety of drug delivery systems. For a brief review of present methods for drug delivery, see, Langer, *Science* 249:1527–1533 (1990), which is incorporated herein by reference. Preferably, the pharmaceutical compositions are administered parenterally, i.e., intraarticularly, intravenously, subcutaneously, or intramuscularly.

The subject peptides may be bound to a liposome or a bilayer lipid membrane or be encapsulated in a liposome. Various techniques are available for joining a peptide or protein to a lipid, particularly a phospholipid to provide for the presence of the peptide or protein on the liposome surface. Phosphatidyl choline, phosphatidyl ethanolamine, or other lipid may be used with a bifunctional linking agent, such as MBSE, glutaraldehyde, methyldithiobenzoic acid, or the like.

The formation of liposomes with conjugated proteins is well known. Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation halflives are typically desirable for therapeutic and diagnostic uses. For instance, liposomes which can be maintained from 8, 12, or up to 24 hours in the bloodstream are particularly preferred.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serve to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4, 837,028, incorporated herein by reference.

Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxianine, are preferred.

A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, all of which are incorporated herein by reference. One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component, and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug or peptides of the invention at a concentration which is desired in the interior volume of the liposomes in the final liposome suspension. Typically the drug or peptide is at concentration between 10–100 mg/ml in a buffered saline solution.

Following liposome preparation, the liposomes may be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposome to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more drug in a free (non-encapsulated) form.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a replacement medium. Alternatively, gel filtration can be used to separate large liposome particles from solute molecules.

Following the above treatment, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposomes comprising the peptides of the invention may be administered parenterally or locally in a dose which varies according to, e.g., the manner of administration, the drug being delivered, the particular disease being treated, etc.

The therapeutic dosage of the peptides of the present invention will vary according to, for example, the particular use for which the treatment is made, the manner of administration of the peptides, the health and condition of the patient, and the judgment of the prescribing physician. For example, for the prevention of allograft rejection with a peptide of the present invention, the dose will typically be the range of about 50 µg to about 2,000 mg per day, preferably about 5 mg to about 700 mg per day, for a 70 kg patient.

The subject peptides, by themselves or as conjugates, may be prepared as formulations in pharmaceutically acceptable media, for example saline, PBS, and glucose, generally at a pharmacologically effective dose, the concentrations of which will be determined empirically in accordance with conventional procedures for the particular purpose. The additives may include bactericidal agents, stabilizers, buffers, or the like. The amount administered to the host will vary depending upon what is being administered, the purpose of the administration, such as prophylaxis or therapy, whether inhibition or activation is desired, the state of the host, the manner of administration, and the like. In order to enhance the half-life of the subject peptide or subject peptide conjugates, the peptides may be encapsulated, introduced into the lumen of liposomes, prepared as a colloid, or other conventional techniques may be employed which provides an extended lifetime of the peptides.

The pharmaceutical compositions are intended for parenteral, topical, oral or local administration, such as by aerosol or transdermally, for prophylactic and/or therapeutic treatment. The compositions are suitable for use in a variety of drug delivery systems. Preferably, the pharmaceutical compositions are administered parenterally, e.g., intravenously. Thus, the invention provides composition for parenteral administration which comprise an immunomodulatory peptide dissolved or suspended in an acceptable carrier, preferably an aqueous carrier, e.g., water, buffered water, 0.4% saline, 0.3% glycine, hyaluronic acid and the like. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The compositions may contain pharmaceutically acceptable auxiliary substances as required to approximate physiological conditions, such as pH adjusting and buffering agents, tonicity adjusting agents, wetting agents, detergents and the like, for example, sodium acetate, sodium lactate, sodium chloride, potassium chloride, calcium chloride, sorbitan monolaurate, triethanolamine oleate, etc.

The concentration of immunomodulatory peptides in the pharmaceutical formulations can vary widely, i.e., from less than about 0.01%, usually at or at least about 5% to as much as 50 to 75% by weight and will be selected primarily by fluid volumes, viscosities, etc., in accordance with the particular mode of administration selected. Thus, a typical pharmaceutical composition for intravenous infusion could be made up to contain 250 ml of sterile Ringer's solution, and 10 mg of peptide.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, preferably 25–75%.

For aerosol administration, the immunomodulatory peptides are preferably supplied in finely divided form along with a conventional non-toxic surfactant and a suitable propellant. Typical percentages of peptides are 0.01%–20% by weight, preferably 1%–10%; and of surfactant from 0.1%–20% by weight, preferably 0.25%–5%.

Two or more peptides of the invention may be combined to form a peptide "cocktail" under certain circumstances for increased efficacy. The peptides of the invention may also be used in conjunction with other pharmaceutically active agents. For instance, other immunosuppressive agents such as antibodies to the α3 domain (e.g., as described in Ozato et al., supra), T cell antigens (e.g., OKT4 and OKT3), antithymocyte globulin, as well as chemotherapeutic agents such as cyclosporine, glucocorticoids, azathioprine, prednisone and the like may be used in conjunction with the peptides.

The following examples are offered by way of illustration and not by limitation.

EXAMPLES

1. Synthesis of Immuno-modulating Peptides

A synthetic peptide corresponding to residues 222–235 of the α3 domain of human HLA class I molecules (having the sequence EDQTQDTELVETRP (SEQ. ID No. 2) and designated HLAI.222–235) was prepared by standard peptide synthesis techniques as described in e.g., Merrifield, *Science* 232:341–347 (1986), Barany and Merrifield, *The Peptides,* Gross and Meienhofer, eds., N.Y., Academic Press, pp. 1–284 (1979); and Stewart and Young, *Solid Phase Peptide Synthesis,* Rockford, Ill., Pierce, 2d Ed. (1984), incorporated by reference herein.

2. Inhibition of Alloreactive and Virus-specific CTL Activation

The peptide prepared according to Example 1 was used to reduce the differentiation of mature CTLs from CTL precursors, as determined by limiting dilution analysis (LDA). The assay procedure is described in Salter et al., supra. Briefly, peripheral blood lymphocytes from normal human donors were isolated by centrifugation over Ficoll-Hypaque and cultured at the indicated number with $3\times10^3$ irradiated (10,000 R) EBV cells (HLA-A2,B27). For enumeration of influenza-specific CTL, 5 mcg/ml of the influenza nucleoprotein ("INF-NP") peptide was added to each culture. For a description of HLA B27 cells and the INF-NP peptide, see, Huet et al., *Int. Immunol.,* 2:311–316 (1990), which is incorporated herein by reference.) Twenty-four replicates were set up for each point. Cultures were supplemented with 200 mcg/ml of HLAI.222–235 peptide (o) or the HLA A2.1 $60\geq84$ peptide (X) and incubated for 7 days. Duplicate aliquots were tested for lysis of $^{51}$Cr-labelled HLA-A2.1 CIR or HLA-B27 CIR in a 4-hour assay. For influenza-specific CTL, 2 mcg/ml of INF-NP 383–394 was added to the cytotoxicity assay. CTL precursor frequency was determined as described in Salter et al., supra.

Figure 1A:
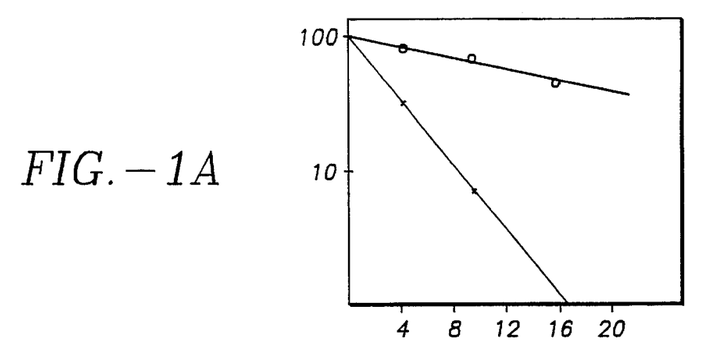
FIGS. 1A, 1B, 1C and 1D show the effect of peptides of the invention on the differentiation of CTL as measured by limiting dilution analysis. The FIG. 1A target is HLA-A2-1. The FIG. 1B target is HLA-B27. The FIG. 1C target is HLA-B27+INF-NP peptide. The FIG. 1D target is HLA-A2-1.
Figure 1B:
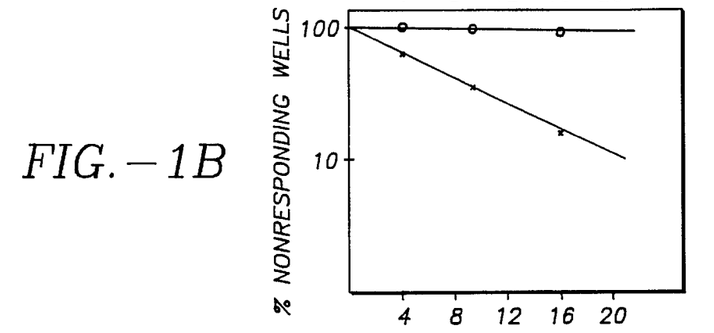
Figure 1C:
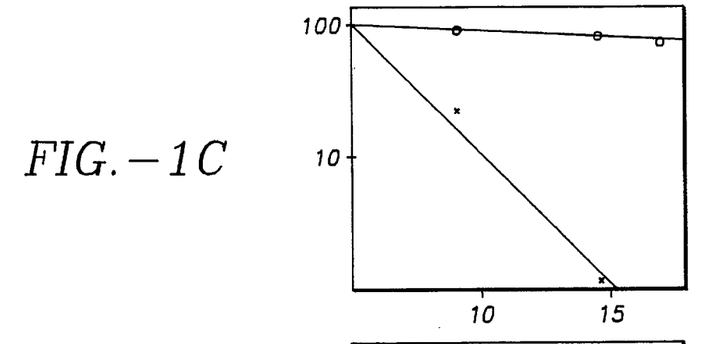

As is shown in FIGS. 1A, 1B and 1C, the HLAI.222–235 peptide effectively blocked CTL generation for both allogeneic and influenza-specific responses, whereas HLA A2.1 60–84 was not effective. These results indicate that interaction of CD8 with MHC class I is critical to activation and differentiation of resting CD8* T cells. These findings further suggest that resting "memory" cells are as CD8-dependent as naive cells, since both recall (influenza-specific) and naive (allospecific) responses were inhibited by the HLAI.222–235 peptide.

Figure 1D:
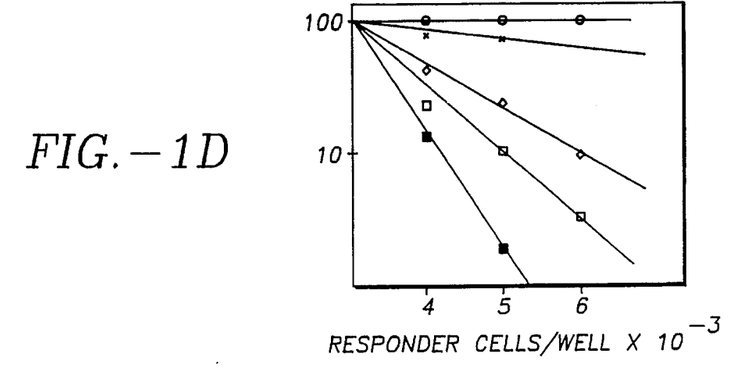

A dose-dependence curve is typically performed to determine the optimal concentration of the immunomodulating peptides for a particular use. In this example, we determined the effect of various concentrations of the HLAI.222–235 peptide on the generation of HLA-A2.1-specific CTLs. The HLAI.222–235 peptide at 200 (o) 100 (x), 50 (◊), or 25 (□) mcg/ml); or the INF NP 383–394 (■) at 200 mcg/ml) was added at the initiation of the 7-day limiting dilution culture as described above. Thus, inhibition in this system was dose-dependent, with essentially complete blockade at 200 mcg/ml (FIG. 1D).

3. Effect of Adding Peptide at Different Stages During Culture

In Example 2, the peptide was added at the beginning of the seven day culture; but it is also possible to add the immunomodulating peptide somewhat before or after exposure to the stimulating cells. We compared the effect of adding the peptide at the initiation of the seven day culture and 24 and 48 hours after initiation. The assays were performed as described above.

Maximum reduction in CTL precursor frequency was observed when the HLAI.222–235 peptide was added at the initiation of the 7-day culture (pCTL frequency: 1/33,723 for HLAI.222–235 vs 1/10,999 for control); intermediate inhibition was demonstrable when the peptide was added 24 hours later (pCTL frequency: 1/16,946), and minimal or no inhibition was observed when the peptide was added at 48 hours or later (pCTL frequency: 1/11,862). The reduction in CTL precursor frequency was sequence-specific, since similarly prepared peptides (HLA A2.1 60–84 and INF NP) had no effect.

4. Effect of the HLA Peptide on Mature Cells

Figure 2:
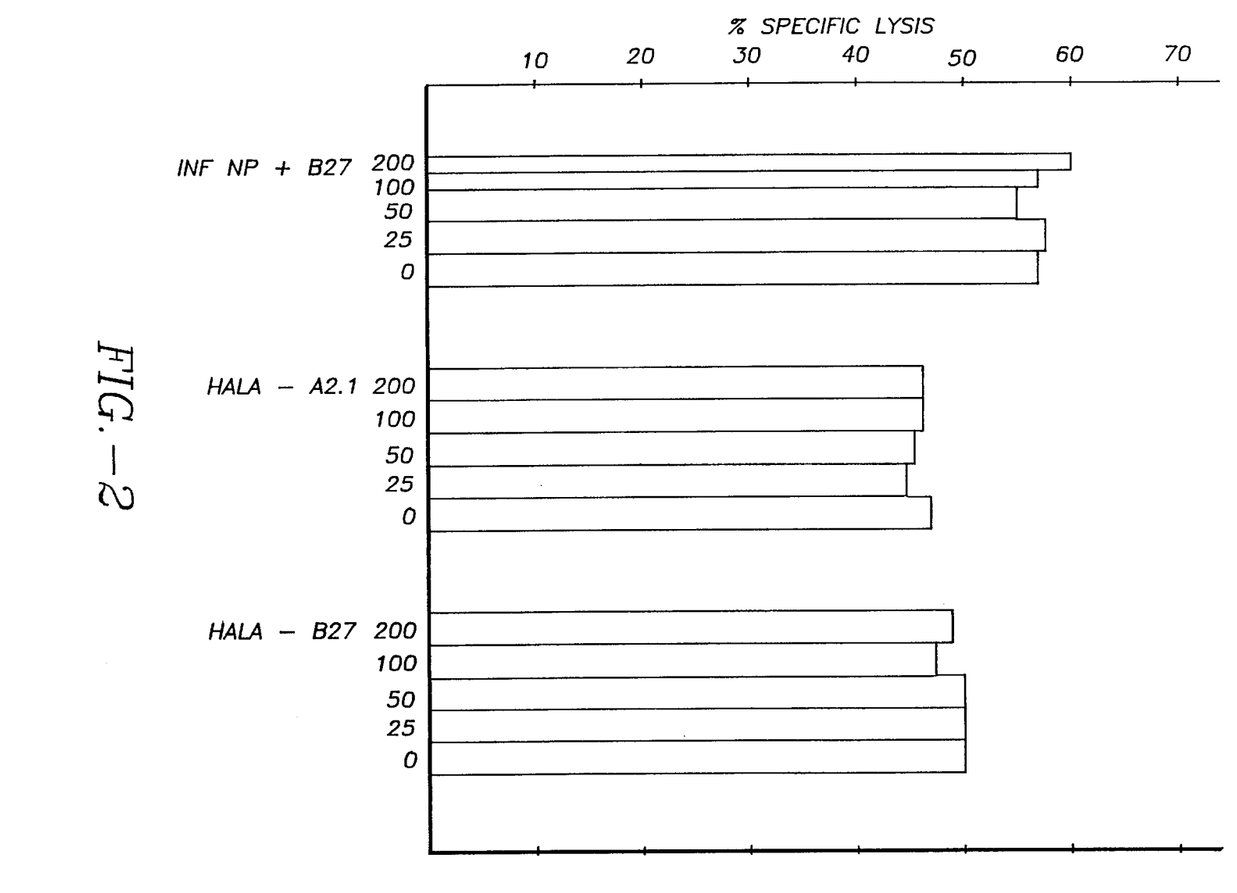
FIG. 2 demonstrates that peptides of the invention have no effect on lysis by mature CTL.

It is also possible to assay the effect of the peptides on mature effector CTLs. The HLAI.222–235 peptide had no effect on cultured CTL which were CD8-dependent or independent (FIG. 2), as judged by inhibition of lysis in a standard 4-hour cytotoxicity assay, indicating that the CD8 Class I interaction plays a less critical role for mature, activated CTL or that the confirmation of the CD8 molecule on cultured CTL alters the binding site for the HLAI.222–235 peptide.

5. The Effect of the HLA Peptide on Primary Proliferative Responses to Alloantigen and Mitogen.

Figure 3:
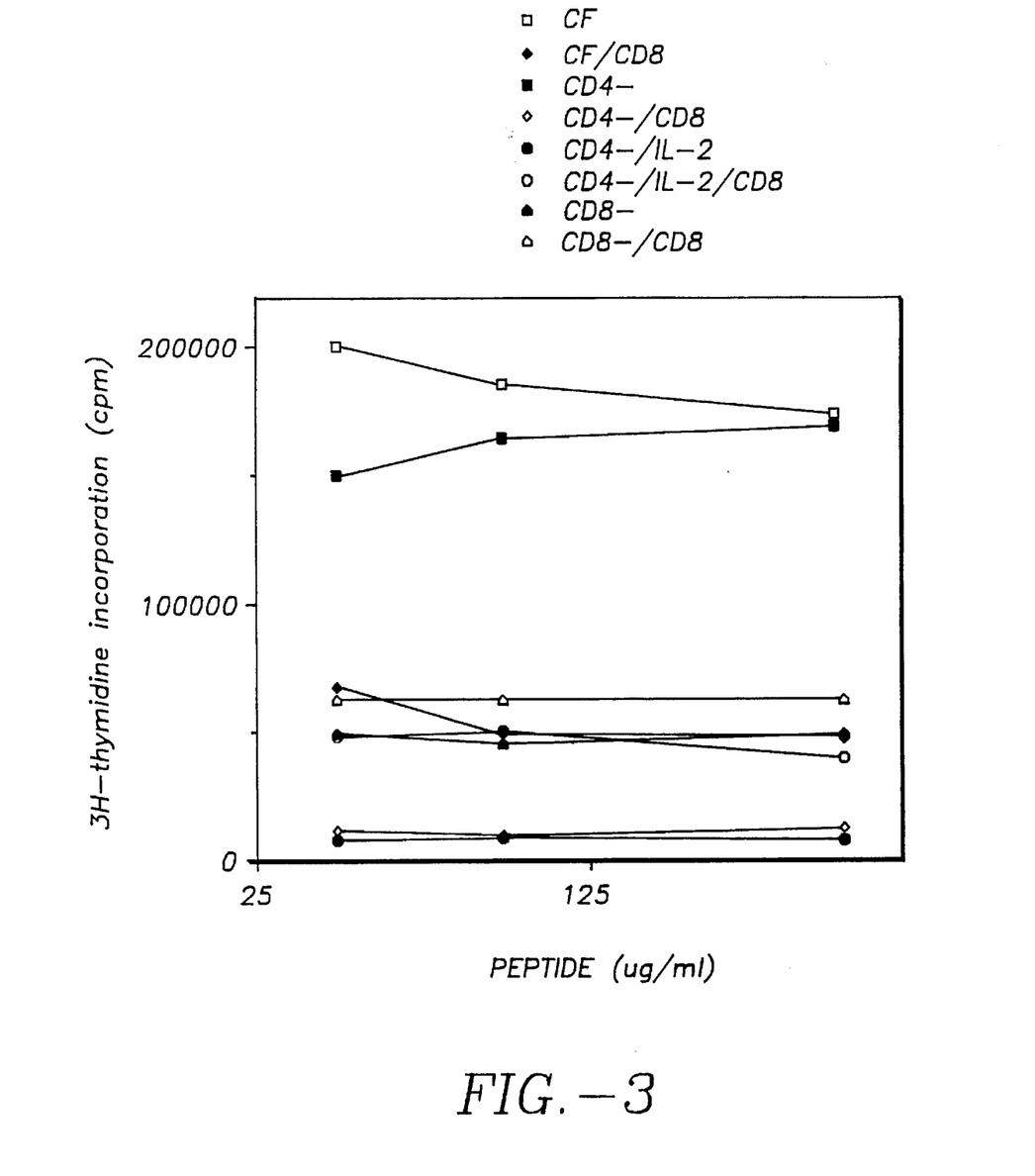
FIG. 3 shows that peptides of the invention do not block alloantigen-induced proliferation of resting peripheral blood lymphocytes.

As shown in FIG. 3, the HLAI.222–235 peptide does not block alloantigen-induced proliferation of resting PBL. PBL ($5\times10^5$) from a normal donor were co-cultured with $3\times10^3$ irradiated EBV cells. In some cases PBL were first depleted of CD4+cells (◊, ♦) or CD8 +cells (▲, △) by passage over anti-CD4 or anti-CD8 antibody-coated plates. Depletion was >95% efficient, as judged by FACS analysis. In some cases (■,□), cultures of CD4-depleted cells were supplemented with T cell conditioned media. The HLAI.222–235 peptide was added at the initiation of culture at the indicated concentration. After 6 days, 1 mcg/L H-thymidine was added to each well, and cultures were harvested 16 hours later.

The examples above demonstrate the ability of the peptides of the present invention to inhibit differentiation of CTL precursors. The invention has been described in these examples and the above disclosure in some detail for the purposes of clarity and understanding. It will be apparent, however, that certain changes and modifications may be practiced within the scope of the appended claims.

What is claimed is:

1. A method of inhibiting the differentiation of a cytotoxic T-lymphocyte (CTL) precursor to a mature CTL specific for a foreign antigen, the method comprising:

before or within 24 hours after exposure to a foreign antigen, effecting the contact of human cytotoxic T-lymphocyte precursors with an effective differentiation inhibiting dose of a peptide of at least about 7 residues having the amino acid sequence of an MHC Class I α3 region, between residues 222–235;

wherein differentiation of said CTL precursor to a mature CTL specific for said foreign antigen is inhibited.

2. The method of claim 1, wherein the peptide has the amino acid sequence EDQTQDTELVETRP (SEQ. ID No. 2).

3. The method of claim 1, wherein the peptide has the amino acid sequence DQTQDTE (SEQ ID No. 1).

4. The method of claim 1 wherein said precursors are contained in an animal subject and said effecting is by administering said peptide to the subject.

5. The method of claim 4 wherein said subject is an allograft recipient.

* * * * *

UNITED STATES PATENT AND TRADEMARK OFFICE
CERTIFICATE OF CORRECTION

PATENT NO. : 5,620,956
DATED : April 15, 1997
INVENTOR(S) : Carol Clayberger et al It is certified that error appears in the above-indentified patent and that said Letters Patent is hereby corrected as shown below:

Column 1, line 2,

--This invention was made with Government support under Contract No. CA47609 awarded by the National Institutes of Health. The Government has certain rights in this invention.--

Signed and Sealed this

Sixteenth Day of September, 1997

Attest:

BRUCE LEHMAN

Attesting Officer

Commissioner of Patents and Trademarks